United States Patent [19]

Grünhoff et al.

[11] Patent Number: 4,746,071

[45] Date of Patent: May 24, 1988

[54] PROCESS FOR CRACKING BLOSSOM POLLEN

[75] Inventors: Ulrich Grünhoff; Lutz Urbat, both of Bad Hönningen, Fed. Rep. of Germany

[73] Assignee: Kohlensaeurewerk Deutschland GmbH, Bad Hoenningen, Fed. Rep. of Germany

[21] Appl. No.: 839,272

[22] Filed: Mar. 13, 1986

[30] Foreign Application Priority Data

Mar. 19, 1985 [DE] Fed. Rep. of Germany ....... 3509759

[51] Int. Cl.$^4$ ............................................. B02C 9/04
[52] U.S. Cl. ............................................. 241/2; 241/1; 241/7; 241/8; 241/23; 241/30
[58] Field of Search ............ 241/1, 2, 7, 8, 17, 241/23, 30

[56] References Cited

U.S. PATENT DOCUMENTS

| 1,512,466 | 10/1924 | Iff | 241/2 |
| 1,789,354 | 1/1931 | Dorner | 241/8 |
| 1,849,786 | 3/1932 | Bloede et al. | 241/8 X |
| 3,361,368 | 1/1968 | Reed | 241/23 X |
| 3,679,139 | 7/1972 | Schneyour et al. | 241/2 |
| 4,004,037 | 1/1977 | Connick | 241/8 X |
| 4,031,199 | 6/1977 | Nieschulz et al. | 241/2 X |
| 4,076,851 | 2/1978 | Tunoda | 241/7 X |
| 4,132,161 | 1/1979 | Helwig . | |

FOREIGN PATENT DOCUMENTS

| 2020655 | 11/1970 | Fed. Rep. of Germany | 241/2 |
| 2922485 | 12/1980 | Fed. Rep. of Germany . | |
| 3347152 | 7/1984 | Fed. Rep. of Germany . | |
| 1003067 | 3/1952 | France . | |
| 2030019 | 10/1970 | France . | |

Primary Examiner—Howard N. Goldberg
Assistant Examiner—Joseph M. Gorski
Attorney, Agent, or Firm—Foley & Lardner, Schwartz, Jeffery, Schwaab, Mack, Blumenthal & Evans

[57] ABSTRACT

A process and apparatus for releasing blossom pollen from its outer skin by a combination of drying and size reduction pressure treatment steps.

8 Claims, 2 Drawing Sheets

PROCESS FOR CRACKING BLOSSOM POLLEN

BACKGROUND OF THE INVENTION

This invention relates to a process for cracking blossom pollen and to an apparatus for carrying out this process.

Because of their content of valuable constituent materials, blossom pollen preparations find many applications as revitalization agents, food supplements and medicaments. However, upon direct administration of pollen, only a very low bioavailability is achieved because the individual grains of pollen are surrounded by a resistant outer skin (Speroderm) which is not broken down in the human digestive system. It is possible to break down the outer skin by chemical reactions in order to recover the constituent materials. This procedure is unsatisfactory because, for example, residues of the chemicals remain in the end product, a decrease in value arises through losses of valuable constituent materials and also taste changes occur.

German Pat. No. 29 22 485 discloses another approach for destroying the pollen skin to release the pollen by means of a cold milling process. This process also has disadvantages. First, the degree of release which is achieved is not satisfactory. Second, a powder is obtained which after only brief storage hardens to a rigid mass which must be remilled or broken down again.

SUMMARY OF THE INVENTION

It is the object of the invention to provide a new process and apparatus for cracking pollen or releasing blossom pollen from its outer skin.

Another object of the invention is to provide a process and apparatus for releasing blossom pollen which avoid the use of chemicals that may adversely affect the end product.

A further object of the invention is to provide a process and apparatus for releasing blossom pollen which minimize losses of valuable constituent materials.

It is also an object of the invention to provide a process and apparatus for releasing blossom pollen which reduce the likelihood of undesirable taste changes.

Still another object of the invention is to provide a process and apparatus for releasing blossom pollen which achieve a high degree of release of the valuable constituents from the outer skin.

An additional object of the invention is to provide a process and apparatus for releasing blossom pollen which produce a product with better storage stability.

These and other objects of the invention are achieved by providing a process for releasing blossom pollen comprising the steps of:

(a) drying the blossom pollen in a first treatment stage, and (b) subjecting the desired blossom pollen to a particle size reducing pressure treatment.

In another aspect of the invention the objects are achieved by providing apparatus for releasing blossom pollen comprising means for drying pollen particles, a pressure chamber, means for supplying pressure gas to the pressure chamber, a decompression chamber and pressure release valve means communicating between said pressure chamber and said decompression chamber.

BRIEF DESCRIPTION OF THE DRAWINGS

The invention will be described in further detail with reference to the accompanying drawings wherein.

DETAILED DESCRIPTION OF PREFERRED EMBODIMENTS

Figure 1:
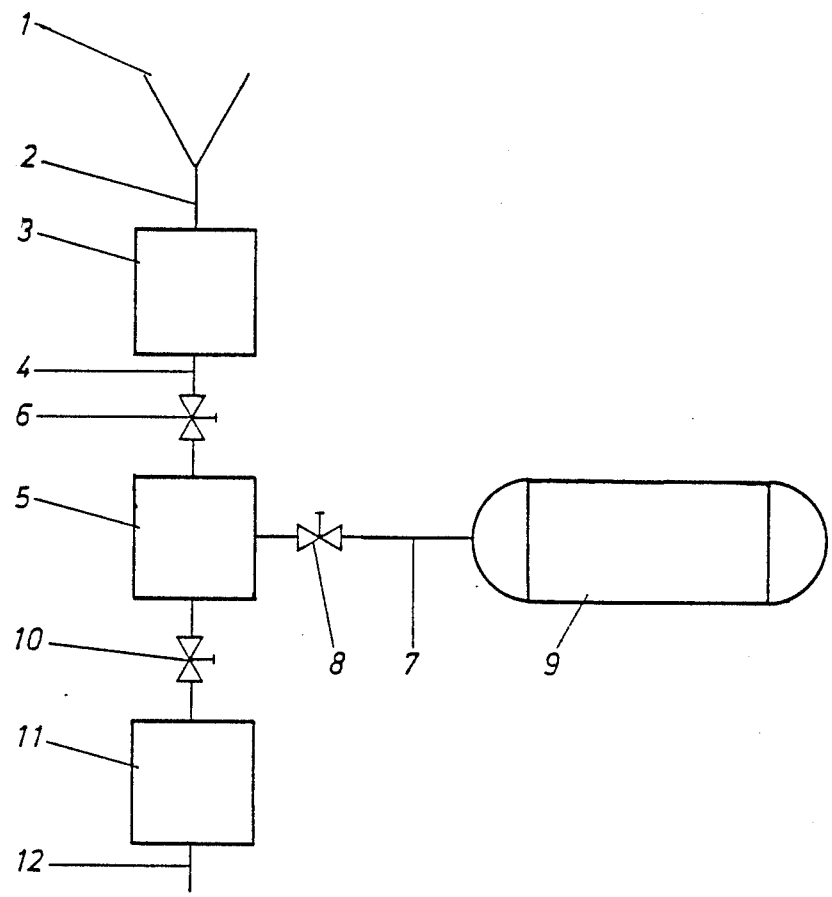
FIG. 1 is a schematic illustration of apparatus for carrying out the pollen releasing process of the invention.
Figure 2:
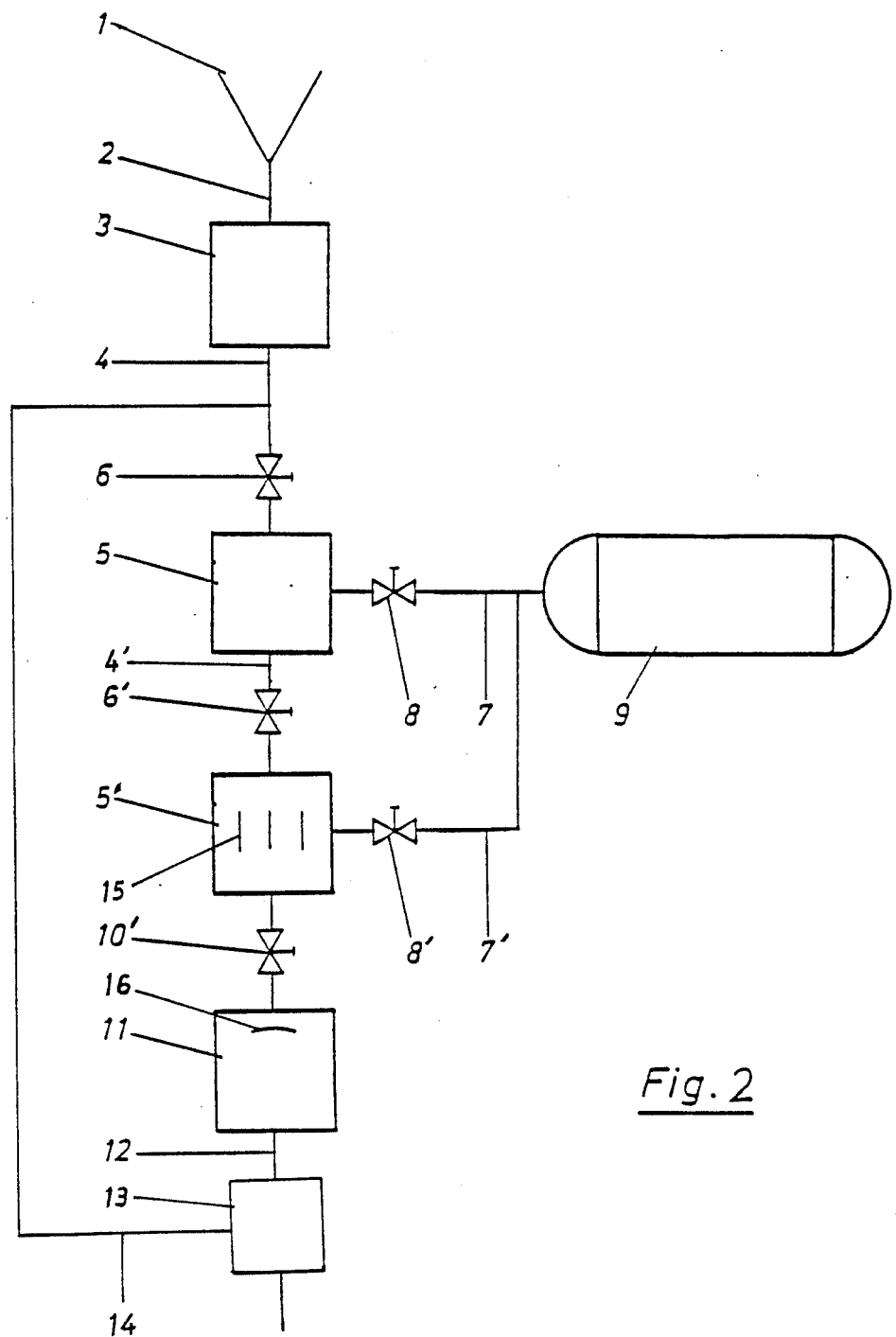
FIG. 2 is a schematic illustration of a modified apparatus for releasing blossom pollen.

The invention comprises a process for unlocking or releasing blossom pollen from its outer skin which is characterized in that in a first stage blossom pollen is subjected to a drying process, and subsequently the dried blossom pollen is subjected to a particle size reduction pressure treatment in a second stage.

The drying in the first stage should take place gently. As a result of the drying step, the moisture content of the pollen grains is adjusted to not greater than about 8 percent by weight. Preferably the moisture content is adjusted to from 1 to 5 percent by weight. The drying energy should be regulated in such a manner that the temperature of the material being dried does not exceed 50° C.

Suitably mild drying processes are known to persons skilled in the drying air. Particularly suitable processes include vacuum drying, lyophilization or microwave drying. Microwave drying is especially suitable for use in the combination process of the invention. With this drying process, drying times of up to 5 minutes are sufficient to achieve the desired moisture content.

The pollen may be cooled after the drying step. This measure is particularly recommended if the pollen has been heated to a temperature near the aforementioned maximum temperature limit and/or if the subsequent particle size reduction pressure treatment is not carried out with an inert gas.

The particle size reduction pressure treatment (cell-cracking process) carried out in the second step is known and is described, for example, in French Published Patent Application No. FR-A 2 030 019, in German Offenlegungsschrift No. DE-OS 26 32 045 or in German Offenlegungsschrift No. DE-OS 33 47 152.

The size reduction pressure treatment basically comprises pressurizing the material which is to be reduced in size with a pressure gas in a pressure chamber and abruptly emptying the material through a decompression device, e.g. a pressure release valve, into a decompression chamber. Devices such as guide vanes, deflectors, etc., may be arranged in a known manner in the decompression chamber.

Conventional gases may be utilized as the pressure gas. The use of inert gases, i.e. gases which do not react with the pollen material in any undesired fashion, is preferred. Examples of suitable gases include carbon dioxide, nitrogen, noble gases, sulfur hexafluoride, halocarbons of fluorine and/or chlorine which are gaseous at room temperature, methane, ethane, propane, etc. It is particularly preferred to use carbon dioxide as the pressure gas.

Pressures of at least 30 bar are used in the pressure treatment. Preferably pressures of at least 40 bar are used.

Additional process steps such as separating steps (e.g. screening, air separation, etc.) may be carried out in conjunction with the size reduction pressure treatment if desired.

It is also possible to improve upon the degree of size reduction achieved in a single-stage treatment either by multi-stage treatment or by recycling coarse particles.

Surprisingly, it has been found that the aforedescribed combination of process steps produces outstanding results. Experimental attempts to release blossom pollen by only a size reduction pressure treatment often resulted in good release of the pollen, but caking of the cracked pollen was also found to occur.

According to the process of the invention there is produced a well released, sensorily unchanged, storage stable, loose particle pollen product which, if an inert gas, particularly carbon dioxide, is used as the pressure gas, also can be packed at the same time in a protective gas atmosphere. In addition, if carbon dioxide is used, a size reduction pressure treatment which is especially gentle on the constituent materials and/or an especially good release can be achieved by varying the density of the carbon dioxide.

The invention also relates to an apparatus for carrying out the process of the invention. Such an apparatus is illustrated schematically in FIG. 1.

Blossom pollen is supplied to a drying stage 3 via a feeder device 1 and a conduit 2. In the preferred embodiment drying stage 3 is a microwave drying station. From drying stage 3 the dried blossom pollen is conveyed through a conduit 4 to a pressure chamber 5. Thereafter locking valve 6 is closed, and pressure gas is introduced from reservoir 9 through conduit 7 and valve 8. After closing of valve 8, the pressure release valve 10 is opened and the contents of pressure chamber 5 are emptied into the decompression chamber 11. The unlocked or released product can be withdrawn through conduit 12.

In further embodiments of the apparatus of the invention as shown in FIG. 2 there may be provided a second pressure chamber 5' or further pressure chambers. The subsequent pressure chambers are provided with supply and pressure gas conduits 4' and 7', locking devices or valves 6' and 8', and pressure release valves 10' similar to those provided for pressure chamber 5 and are arranged between pressure chamber 5 and final decompression chamber 11. Each subsequent pressure chamber 5' thereby simultaneously serves as a decompression chamber for the preceding pressure chamber 5. If desired, size classifying means 13 such as a screening device or an air separator and a recycle conduit 14 leading back to the pressure chamber 5 may be provided for separating and recycling a coarse particle fraction. If desired, devices such as guide vanes 15, deflectors 16, etc., also may be installed in the decompression chambers.

EXAMPLE

Blossom pollen was released in an apparatus corresponding to FIG. 1. The moisture content of the starting material amounted to from 12 to 15 percent by weight. After drying by microwave treatment (Product temperature approx. 50° C., residence time approx. 2 minutes) the moisture content was 5 percent by weight.

Subsequent to the drying step, a two-stage size reduction pressure treatment ($CO_2$, 50 bar) was carried out. After the first stage the fine particle fraction (size less than 150$\mu$) was 80 percent by weight. After the second stage a fine particle proportion amounting to 91 percent by weight was obtained.

In a comparison test which was carried out in the same way except without drying, a fine particle fraction of only 35 percent by weight was obtained after the first stage, and a fine particle proportion of 48 percent by weight was obtained after the second stage.

The product of the invention remained as loose granules after packaging, while the product of the comparison test started to cake after approximately one hour.

The foregoing description and examples have been set forth merely to illustrate the invention and are not intended to be limiting. Since modifications of the described embodiments incorporating the spirit and substance of the invention may occur to persons skilled in the art, the scope of the invention should be limited solely with respect to the appended claims and equivalents.

We claim:

1. A process for cracking grains of blossom pollen comprising the steps of:

(a) drying the blossom pollen in a first treatment stage at a temperature not exceeding 50° C. to a moisture content of not greater than 8 percent by weight, and (b) pressurizing the dried blossom pollen with a gas which is inert to the pollen in a subsequent treatment stage, and then abruptly depressurizing the pollen, thereby fracturing the pollen grains.

2. The process for cracking grains of blossom pollen according to claim 1, wherein said drying is effected by a drying method selected from the group consisting of vacuum drying, lyophilization and microwave drying.

3. The process for cracking grains of blossom pollen according to claim 2, wherein said drying is effected by microwave drying.

4. The process for cracking grains of blossom pollen according to claim 3, wherein said drying is carried out for a period of up to 5 minutes.

5. The process for cracking grains of blossom pollen according to claim 1, wherein said inert gas is carbon dioxide.

6. The process for cracking grains of blossom pollen according to claim 1, wherein said pressurizing is carried out at a pressure of at least 30 bar.

7. The process for cracking grains of blossom pollen according to claim 6, wherein said pressurizing is carried out at a pressure of at least 40 bar.

8. The process for cracking grains of blossom pollen according to claim 1, wherein said pressurizing is carried out in a plurality of stages.

* * * * *